United States Patent
Trainer

[19]

[11] Patent Number: 6,084,665
[45] Date of Patent: Jul. 4, 2000

[54] OPTICAL SENSOR FOR DETECTING THE DEW POINT OF AN ATMOSPHERE

[75] Inventor: Michael N. Trainer, Telford, Pa.

[73] Assignee: Honeywell International Inc., Morristown, N.J.

[21] Appl. No.: 09/145,068

[22] Filed: Sep. 1, 1998

[51] Int. Cl.[7] .......................... G01N 21/01; G01N 21/55; G02B 6/42

[52] U.S. Cl. .......................... 356/244; 356/244; 356/445; 250/227.25

[58] Field of Search .................................. 356/244, 246, 356/445, 446; 250/216, 227.11, 227.24, 227.25

[56] References Cited

U.S. PATENT DOCUMENTS 4,950,885  8/1990  Kershaw ............................ 250/227.25

Primary Examiner—Frank G. Font
Assistant Examiner—Michael P. Stafira
Attorney, Agent, or Firm—Anthony Miologos

[57] ABSTRACT

An optical sensor for detecting the dew point of an atmosphere is disclosed for use with an optical measurement system. The optical measurement system includes a source of light energy, a light detector, and a light energy conduction arrangement for directing light energy from the source of light energy to the optical sensor. The light energy conduction arrangement also returns light energy from the optical sensor to the light detector. The optical sensor of the present invention includes a substrate located within the atmosphere and a first waveguide located on a surface of the substrate. The first waveguide includes a first end optically connected to the light energy conduction arrangement arranged to receive thereat light energy from the source of light energy and to direct thereat light energy to the light detector. A second waveguide is located on the substrate first surface parallel to and in a spaced relationship to the first waveguide. The second waveguide includes an end that is prepared as a reflecting surface. A means for cooling is attached to the substrate and is arranged to cool the optical sensor to a temperature below the ambient temperature of the atmosphere, to cause water vapor that may be contained in the atmosphere to condense and form deposits of water between the first and second waveguides. The water deposits form an evanescent region in the area of the condensate, coupling the light energy from the first waveguide to the second waveguide. The light energy entering the second waveguide is reflected off of the second waveguide's reflecting surface and is directed back to the evanescent region, where the light energy is coupled back to the first waveguide and the light energy conduction arrangement for transmission to the light detector.

8 Claims, 2 Drawing Sheets

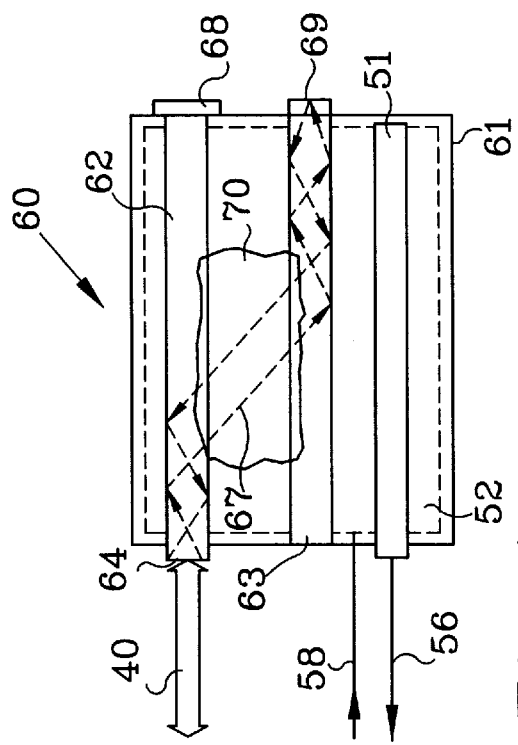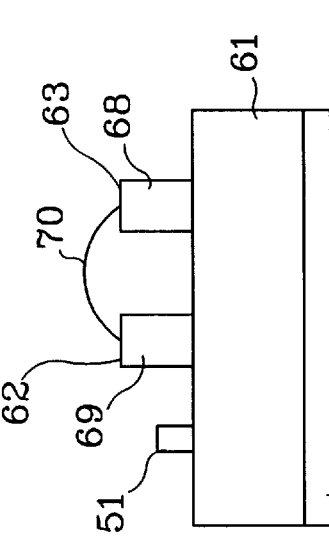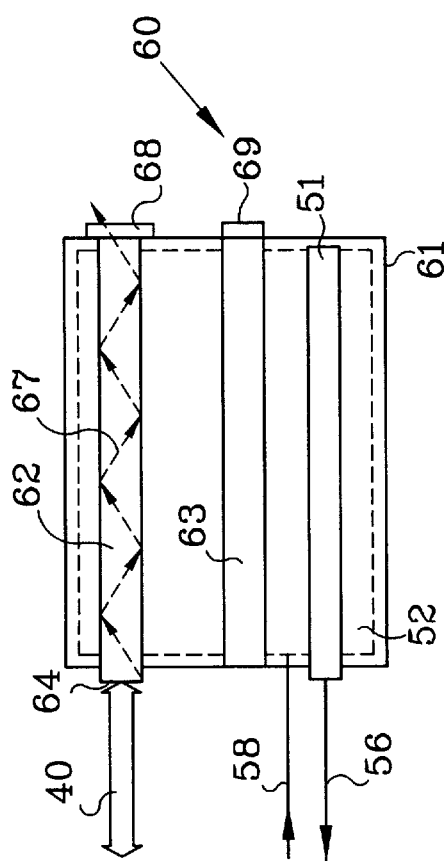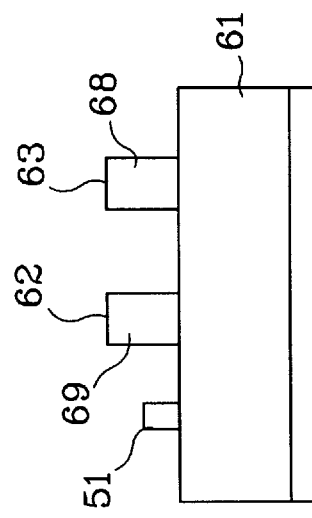

OPTICAL SENSOR FOR DETECTING THE DEW POINT OF AN ATMOSPHERE

CROSS-REFERENCE TO RELATED APPLICATIONS

This present application is related to applicant's co-pending patent application Ser. No. 09/145,072, entitled, "A Fiber Optic Hygrometer Apparatus and Method", filed on an even date herewith and assigned to a common assignee with the present invention.

BACKGROUND OF THE INVENTION

1. Field of the Invention

The present invention relates generally to moisture sensitive transducers and, more specifically, to an optical sensor used in sensing the dew point of an atmosphere in a process environment.

2. Discussion of the Related Art

Many methods of sensing the humidity levels present in a gaseous atmosphere are based upon inferring the moisture content of a sample from an output of a moisture-sensitive transducer. Such methods may be subject to such inherent limitations as a non-linear variation of the output parameter with humidity, drift, temperature sensitivity, hysteresis and aging. The limitation of temperature relates to the fact that the water-holding capacity of a gas varies with temperature so that only a relative humidity rather than an absolute measurement is provided. Relative humidity can be related to absolute humidity by using known conversion algorithms, such as the Goff-Gratch equation. However, this algorithmic solution can not be conveniently embodied in a linear circuit.

One method presently known and used extensively in industry for providing absolute humidity readings is to use chilled mirror hygrometers that provide an indication of dew point or frost point, each of which is a primary measurement of moisture content. The dew point is the temperature at which the partial pressure of a condensate on a surface equals the water vapor partial pressure in a gas. Similarly, frost point is the saturation temperature to which the gas temperature must be cooled at constant pressure so that it will be saturated in respect to ice. Saturation vapor pressure is a unique function of temperature. Therefore, determining the temperature at which water vapor begins to condense on a cool surface is equivalent to a measurement of its partial pressure.

Chilled mirror hygrometers use cooled mirrors as the surface where condensation takes place. Using electro-optic circuitry, a precise determination of the formation of either dew or frost is made. A temperature transducer, such as a platinum resistance transducer, is used to provide the signal indicating the output information.

One of the limitations of using such chilled mirror hygrometers in industrial applications is the inability of the electro-optic elements to differentiate between dew or frost deposits and dirt or soot deposits that may coat the mirror by particulate byproducts of the process being measured. Since dew, as well as contaminants such as dirt deposits, will be measured by the included photosensors as a loss of reflected light, a differentiation between the dew and contaminant conditions must be made to ensure the accuracy of the hygrometer. Prior art responses in dealing with this type of contamination included cleaning procedures that are performed periodically or on an event-dependent basis. Another method employs compensation procedures in the hygrometers operation that "balance" the system. This is done by, in essence, performing a calibration operation to "null" variations in the optic sensitivity scheme due to the contaminant deposited on the mirror. This is accomplished by raising the temperature of the mirror to a temperature higher than the dew point to ensure a dry mirror so that the loss in reflectivity due to the contaminant alone may be measured. Adjustments are than made to the optical sensing circuitry to compensate for any differences in respect to the original calibration values.

Both these methods require taking the hygrometer "off-line", thereby losing the ability to monitor the process while the cleaning or compensation procedures are being performed. Additionally, as the contaminant deposits coating the mirror become more expansive, the compensation procedure explained above requires it be performed more frequently, increasing the time and frequency which the hygrometer must be off-line.

BRIEF SUMMARY OF THE INVENTION

In accordance with the present invention, there is provided an optical sensor for detecting the dew point of an atmosphere for use with an optical measurement system. The optical measurement system includes a source of light energy, a light detector, and a light energy conduction arrangement for directing light energy from the source of light energy to the optical sensor. The light energy conduction arrangement also returns light energy from the optical sensor to the light detector.

The optical sensor of the present invention includes a substrate located within the atmosphere having at least a first planar surface and a first light energy waveguide located on the substrate's first surface. The first waveguide includes a first end and a second end with the first end optically connected to the optical measurement system's light energy conduction arrangement. The first waveguide is arranged to receive light energy from the source of light energy and to direct light energy to the light detector.

A second light energy waveguide is located on the substrate first surface parallel to and in a spaced relationship to the first waveguide. The second waveguide includes an end that is prepared as a reflecting surface. A means for cooling is attached to the substrate and is arranged to cool the optical sensor to a temperature below the ambient temperature of the atmosphere to cause water vapor that may be contained in the atmosphere to condense and form deposits of water between the first and second waveguides. The water deposits form an evanescent region in the area of the condensate, coupling the light energy from the first waveguide to the second waveguide. The light energy entering the second waveguide is reflected off of the second waveguide reflecting surface and is directed back to the evanescent region, where the light energy is coupled back to the first waveguide in the direction of the first waveguide first end. The returned light energy enters the light energy conduction arrangement for transmission to the light detector.

The present invention can also be effectively used to detect and signal the presence of a liquid. As a liquid detector, the optical sensor of the present invention has the substrate located in an area where the presence of a liquid is to be detected. A first light energy waveguide is located on the substrate and is optically connected to the light energy conduction arrangement. The first waveguide is arranged to receive light energy from the source of light energy and to direct light energy back to the light detector. A second light energy waveguide is also located on the substrate in parallel to and in spaced relationship to the first waveguide. The second waveguide further includes an end prepared as a reflecting surface. Responsive to liquid contacting the first and second waveguides, an evanescent region is formed in the area of liquid contact, coupling light energy from the first waveguide to the second waveguide. The light energy entering the second waveguide is reflected off of the reflecting surface and is directed back to the evanescent region, coupling the light energy to the first waveguide in the direction of the first waveguide first end and to the light energy conduction arrangement for transmission to the light detector.

It is, therefore, an object of the present invention to provide a dew point detector that is not affected by contaminants found in the process environment.

It is also an object of the present invention to provide a simple optical sensor that can continuously and effectively monitor the dew point of an atmosphere of a process environment without the need of going "off-line" to clean, compensate or balance the operation of the apparatus.

It is also a further object of the present invention to provide an optical dew point sensor that is less technically complex and, therefore, more operationally reliable than the moisture sensitive transducers currently known.

BRIEF DESCRIPTION OF THE SEVERAL VIEWS OF THE DRAWINGS

Other objects, features, and advantages of the present invention will be apparent from the following description of a preferred embodiment thereof, taken in conjunction with the sheets of drawings, in which:

FIG. 2 is a top plan view of the elements of the optical sensor of the present invention showing the operation of the sensor in the absence of a condensate deposit;

FIG. 3 is a front view of the optical sensor shown in FIG. 2;

FIG. 4 is a top plan view of the elements of the optical sensor of the present invention showing the operation of the sensor with the presence of a condensate deposit; and FIG. 5 is a front view of the optical sensor shown in FIG. 4.

DETAILED DESCRIPTION OF THE INVENTION

Figure 1:
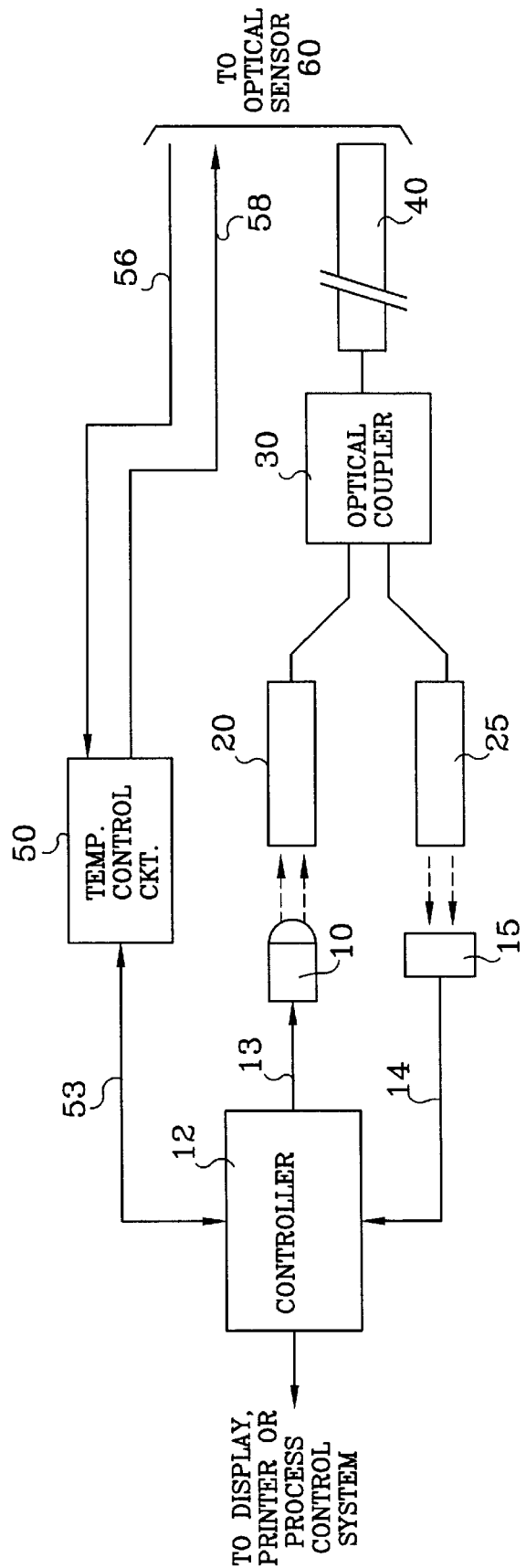
FIG. 1 is a block diagram of an optical measurement system used with the optical sensor of the present invention.

The optical sensor of the present invention is used to advantage with an optical measurement system such as the optical measurement system shown in FIG. 1. The optical measurement system shown is arranged to convey to, and receive from, the optical sensor of the present invention light energy and electrical signals. The optical measurement system shown in FIG. 1 includes a source of light energy 10, optically coupled to a first optical fiber segment 20 that in turn is optically connected to an optical fiber coupler 30. The optical fiber coupler 30 is connected to an optical fiber conductor 40, which extends to and is optically connected to the optical sensor 60 of the present invention. The optical fiber coupler 30 is further connected to a second optical fiber segment 25 with the second optical fiber segment 25 optically connected to a light detector device 15. Both the light source 10 and the light detector device 15 are electrically connected to a controller 12 by signal leads 13 and 14, respectively. The controller 12 is arranged to provide signals to enable and disable the light source 10 and to receive and process the electrical signals from the light detector device 15. The electrical signals from the light detector device 15 represents the intensity or magnitude of the light received by light detector device 15. The controller 12 is further connected to a temperature control circuit 50 via signal path 53. The temperature control circuit 50 is connected via conductors 58 and 56 to a thermoelectric cooler and a temperature sensor, respectively, located on the optical sensor 60. A better understanding of the optical measurement system just described may be had by reference to applicant's co-pending patent application, entitled, "A Fiber Optic Hygrometer Apparatus and Method", Ser. No. 09/145,072, which is incorporated herein by reference.

The optical sensor 60 of the present invention, illustrated in FIGS. 2 and 3 is comprised of a base substrate 61 having a first optical waveguide 62 attached to a top surface of base substrate 61. A second optical waveguide 63 is attached to the top surface of base substrate 61 in a spaced and parallel relationship to optical waveguide 62. The base substrate 61 is composed of any suitable material that will rigidly accept waveguides 62 and 63 thereon and which exhibits a lower refractive index than the waveguides 62 and 63. Additionally, the base substrate 61 does not necessarily require to be the planar structure shown to achieve the results of the present invention. It will be well understood by those skilled in the art that the base substrate 61 provides a means of support for, and one method for the proper spacing between, waveguides 62 and 63 and is shown as a planar structure in this embodiment in order to ease the understanding of the invention. For example, the planar substrate base 61 shown could be substituted by a thermally conductive epoxy compound that exhibits a low refractive index that has waveguides 62 and 63 properly spaced and partially embedded therein. The waveguides 62 and 63 are composed of a transparent material, such as glass or plastic. Most glass waveguides are fused silica and most plastic waveguides are polymethylmethacrylate (PMMA). Both waveguides 62 and 63 of the present invention are unclad structures which conduct light energy internally by a process of total internal reflection (TIR). In such unclad waveguide structures, the majority of the light energy striking the glass-air or plastic-air interface is internally reflected within the waveguide structure. Waveguide 62 further includes a first end surface 64 arranged to accept and optically couple thereat optical fiber conductor 40 from the optical measurement system. A second and opposite end 68 of waveguide 62 is prepared as "beam dump" allowing light energy striking the beam dump surface to be directed out of the waveguide 62.

Waveguide 63 includes an end 69 that has its surface polished and coated with reflecting material. A thermoelectric cooler 52 is attached to a bottom surface of base substrate 61 and is electrically connected to the temperature control circuit 50 via conductor 58. The thermoelectric cooler is disposed to cool or alternatively heat the base substrate 61 and the waveguides 62 and 63. A temperature sensor 51 is attached to the top surface of the substrate and is also electrically connected to the temperature control circuit 50 via electrical conductor 56. The temperature sensor 51 is disposed to measure the temperature of the optical sensor 60 and transmit signals to the temperature control circuit 50 representing the temperature of the optical sensor 60. It will be apparent to those skilled in the art that a thermocouple device could also be used for the temperature sensor 51 illustrated and the invention, therefore, is not limited thereto.

The optical sensor 60 of the present invention is used to advantage by installing the optical sensor 60 within an atmosphere of a process environment whose dew point or moisture content is to be monitored and measured. With renewed reference to FIGS. 1, 2 and 3 the operation of the present invention will now be explained. In a state where the optical sensor is at the same temperature as the atmosphere being measured, a signal from the controller 12 enables light source 10, coupling the light energy radiating from the light source into the first fiber optic segment 20. The light energy is internally reflected through the optical fiber coupler 30 to the optical fiber conductor 40. The light energy is carried by the optical fiber conductor 40 to end 64 of waveguide 62. The light energy entering waveguide 62 is internally reflected within waveguide 62 toward the direction of end 68 and the beam dump. As illustrated by broken lines 67, the majority of the light energy internally reflected within waveguide 62 is directed out of waveguide 62 by end 68. Most of the light energy coupled into waveguide 62 is spilled out of the waveguide, however, a minor portion of light energy may be internally reflected back into optical fiber conductor 40, optical fiber coupler 30 and the second optical fiber segment 25 to the light detector 15. The light detector 15 produces a signal to the controller 12 representing the amount or intensity of light energy returned from the optical sensor 60. In this state, whereby the optical sensor is at the same temperature as the atmosphere, only a minor portion of the light energy transmitted to the optical sensor 60 is returned and the light detector 15 sends to the controller signals representing the reduced level of light energy it receives.

The optical sensor 60 of the present invention uses the phenomenon of evanescence to advantage in providing the sensing and measurement of the moisture content or dew point of a process environment atmosphere. As explained earlier, in unclad waveguide structures the majority of the light energy injected into the waveguide structure and striking a glass-air or plastic-air interface is internally reflected within the waveguide structure. On the other side of this glass-air or plastic air-interface, where the reflection occurs, some of the light exits for a short distance in the physical form of an evanescent field. If water or some other liquid condensate is attached to the exterior of the waveguide at this locality, the index of refraction is changed, causing a greater portion of the internally reflected light energy to be redirected outward from, and to escape from, the waveguide structure. The present invention uses this evanescent phenomenon as a means of detecting or sensing the dew point or moisture content found in the atmosphere of a process environment.

Turning now to FIGS. 4 and 5, the operation used by the present invention to measure the dew point of an atmosphere will now be explained. As explained earlier, with the optical sensor 60 at the same temperature as the surrounding atmosphere, the majority of the light transmitted from the source 10 enters waveguide 62 and is spilled out of beam dump end 68. A minority portion of the light energy coupled into waveguide 62 may be internally reflected back into optical fiber conductor 40 and directed to light detector 15.

To establish the dew point or moisture content of the atmosphere, a command from controller 12 is sent to the temperature control circuit 50, which signals the thermoelectric cooler 52, to begin cooling optical sensor 60. When the base substrate 61 and waveguides 62 and 63 cool sufficiently, any water vapor present within the atmosphere being measured will condense and form deposits of liquid 70 in the region between waveguides 62 and 63. This condensate deposit 70 becomes attached to the outer surfaces between the waveguides 62 and 63, modifying the index of refraction from a glass-air interface, to a glass-water interface and effectively forming a bridge for the light energy to travel between waveguide 62 and 63.

The evanescent phenomenon causes the internally reflected light energy conveyed by waveguide 62 to be redirected and diverted into waveguide 63. Light energy entering waveguide 63 travels in the direction toward the reflecting surface of waveguide end 69. The light energy striking the reflecting surface is internally reflected back into waveguide 63. At the region of the condensate deposit 70 the light energy is redirected back into waveguide 62 in the direction, however, of optical fiber conductor 40. This is illustrated in FIG. 4 by broken lines 67. Some light may still spill from the beam dump end 68; however, the majority of the light energy conducted into waveguide 62 is reflected back from waveguide 63 and transmitted from the optical sensor 60 through optical fiber conductor 40, coupler 30 and second fiber optic segment 25 to light detector 15. Light detector 15 now receives and detects a magnitude of light energy that is greater than the magnitude of light energy it had been receiving before the optical sensor 60 was cooled. Upon the detection of this increased light energy level, the controller 12 signals the temperature control circuit 50 to read the temperature signals from temperature sensor 51, thereby establishing the dew point of the atmosphere of the process environment. The temperature just read is passed from the temperature control circuit 50 to the controller 12, where the controller 12 outputs a signal to a display device, printer or process control system (not shown). Alternatively, the signal output by the controller 12 can be in the form of an alarm signal that can signal a condition requiring immediate attention.

In situations when the ambient temperature of the atmosphere of the process environment is lower than the atmosphere's dew point, the thermoelectric cooler 52 can be used to heat the optical sensor 60 well above the dew point to evaporate any water or liquid deposits 70 that may be attached to waveguides 62 and 63. The cooler 52 is then commanded to cool optical sensor 60 toward the dew point and the dew point temperature ascertained in accordance to the method of the present invention described above.

It will be well understood by those skilled in the art that the present invention can also be effectively used to detect and sense the presence of a liquid or a liquid level. In the detection of a liquid, or of a liquid level, the temperature control circuit 50, thermoelectric cooler 52 and temperature sensor 51 would not be required. Any liquid deposited between light guides 62 and 63 would cause an increase in the magnitude of light energy applied to light detector 15 as explained above. Upon detection by the light detector 15 of an increased light intensity level, a signal can be output by the controller 12 to announce the presence of a liquid or the level of a liquid, for example, in a vessel or container. The present invention provides a simple and effective means for the detection of the water vapor or dew point of a process environment and is insensitive to dust, soot or other contaminants that may collect on the surfaces of the optical sensor 60 due to the contaminants that may be present or inherent within the process environment.

The present invention has been described with particular reference to the preferred embodiments thereof. It will be obvious that various changes and modifications can be made therein without departing from the spirit and scope of the invention as defined in the appended claims.

What is claimed is:

1. An optical sensor for detecting the dew point of an atmosphere for use with an optical measurement system, said optical measurement system including a source of light energy, a light detector, and a light energy conduction arrangement for directing light energy from said source of light energy to said optical sensor and to return light energy from said optical sensor to said light detector, said optical sensor comprising:

a substrate located within said atmosphere having at least a first surface;

a first waveguide located on said substrate's first surface and including a first end and a second end, said first end optically connected to said optical measurement system light energy conduction arrangement, arranged to receive light energy from said source of light energy and to direct light energy to said light detector;

a second waveguide located on said substrate first surface parallel to and in a spaced relationship to said first waveguide, said second waveguide including an end prepared as a reflecting surface; and means for cooling arranged to cool said optical sensor to a temperature below the ambient temperature of said atmosphere to cause water vapor that may be contained in said atmosphere to condense between said first and second waveguides forming an evanescent region in the area of said condensate and coupling said light energy from said first waveguide to said second waveguide wherein said second waveguide's reflecting surface directs said light energy back to said evanescent region, coupling said light energy to said first waveguide first end and to said light energy conduction arrangement.

2. The optical sensor in accordance to claim 1 wherein said optical measurement system further includes a temperature control circuit and said substrate further includes a second surface, and said means for cooling is located on said substrate second surface and is operatively connected to said temperature control circuit, and responsive to signals from said temperature control circuit said means for cooling cools said substrate.

3. The optical sensor in accordance to claim 2 wherein said means for cooling is a thermoelectric cooler and responsive to first signals from said temperature control circuit said thermoelectric cooler cools said substrate.

4. The optical sensor in accordance to claim 3 wherein, responsive to second signals from said temperature control circuit, said thermoelectric cooler heats said substrate.

5. The optical sensor in accordance to claim 1 wherein said first waveguide second end is disposed to direct said light energy that strikes said second end out of said first waveguide, whereby in the absence of said evanescent region a majority of said light energy is conducted through said first waveguide and out of said first waveguide second end.

6. The optical sensor in accordance to claim 2 wherein said optical measurement system further includes a controller operatively connected to said light detector and to said temperature control circuit, and said optical sensor further includes a temperature sensor located on said substrate first surface operatively connected to said temperature control circuit said temperature sensor sends signals to said temperature control circuit representative of the temperature of said optical sensor and, responsive to said light detector receiving light energy from said optical sensor of a predetermined magnitude, said controller reads the temperature of said optical sensor from said temperature control circuit.

7. An optical sensor for detecting the dew point of an atmosphere for use with an optical measurement system, said optical measurement system including a source of light energy, a light detector, and a light energy conduction arrangement for directing light energy from said source of light energy to said optical sensor and to return light energy from said optical sensor to said light detector, said optical sensor comprising:

first light energy guiding means located in said atmosphere optically connected to said light energy conduction arrangement, said first light energy guiding means arranged to receive light energy from said source of light energy and to direct light energy back to said light detector;

second light energy guiding means located in said atmosphere parallel to and in a spaced relationship to said first light energy guiding means, said second light energy guiding means further including an end prepared as a reflecting surface; and means for cooling arranged to cool said first and said second light energy guiding means to a temperature below the ambient temperature of said atmosphere to cause water vapor that may be contained in said atmosphere to condense between said first and second light energy guiding means forming an evanescent region in the area of said condensate and coupling said light energy from said first light energy guiding means to said second light energy guiding means wherein said reflecting surface reflects said light energy striking said reflecting surface back to said evanescent region coupling said light energy back to said first light energy guiding means and to said light energy conduction arrangement and said light detector.

8. An optical sensor for detecting the presence of a liquid for use with an optical measurement system, said optical measurement system including a source of light energy, a light detector, and a light energy conduction arrangement for directing light energy from said source of light energy to said optical sensor and to return light energy from said optical sensor to said light detector, said optical sensor comprising:

a substrate located in an area where the presence of a liquid is to be detected, said substrate having at least a first planar surface;

first light energy guiding means located on said substrate's first surface optically connected to said light energy conduction arrangement, said first light energy guiding means arranged to receive light energy from said source of light energy and to direct light energy back to said light detector;

second light energy guiding means located on said substrate's first surface in parallel to and in spaced relationship to said first light energy guiding means, said second light energy guiding means further including an end prepared as a reflecting surface; and responsive to liquid contacting said first and said first and said second light energy guiding means and an evanescent region is formed in the area of liquid contact coupling said light energy from said first light energy guiding means to said second light energy guiding means wherein said reflecting surface reflects said light energy striking said reflecting surface back to said evanescent region coupling said light energy back to said first energy guiding means and to said light energy conduction arrangement and said detector.

\* \* \* \* \*